United States Patent [19]

Flaugh et al.

[11] Patent Number: 5,302,612
[45] Date of Patent: Apr. 12, 1994

[54] 6-SUBSTITUTED-HEXAHYDROBENZ[C-D]INDOLES

[75] Inventors: Michael E. Flaugh; Michael J. Martinelli, both of Indianapolis, Ind.

[73] Assignee: Eli Lilly and Company, Indianapolis, Ind.

[21] Appl. No.: 68,561

[22] Filed: May 27, 1993

Related U.S. Application Data

[63] Continuation of Ser. No. 883,803, May 13, 1992, abandoned, which is a continuation of Ser. No. 567,986, Aug. 15, 1990, abandoned, which is a continuation-in-part of Ser. No. 482,811, Feb. 26, 1990, Pat. No. 5,204,340.

[51] Int. Cl.$^5$ ............ A61K 31/40; A61K 31/535; C07D 209/90; C07D 295/192
[52] U.S. Cl. ............................ 514/411; 548/436; 544/142; 546/200; 514/232.8; 514/323
[58] Field of Search ............... 548/436; 514/411

[56] References Cited

U.S. PATENT DOCUMENTS

| | | | |
|---|---|---|---|
| 2,809,974 | 10/1957 | Kornfeld et al. | 548/436 |
| 3,336,307 | 8/1967 | Shen | 546/272 |
| 3,671,541 | 6/1972 | Bormann et al. | 548/311.4 |
| 3,674,801 | 7/1972 | Bormann et al. | 548/311.4 |
| 4,057,560 | 11/1977 | Bormann et al. | 548/436 |
| 4,110,339 | 8/1978 | Bach et al. | 548/436 |
| 4,282,240 | 8/1981 | Baldwin et al. | 514/411 |
| 4,576,959 | 3/1986 | Flaugh | 514/411 |
| 4,745,126 | 5/1988 | Leander | 514/411 |
| 4,853,406 | 8/1989 | Rosentreter et al. | 514/411 |
| 4,983,622 | 1/1991 | Flaugh | 514/411 |
| 5,039,820 | 8/1991 | Kress et al. | 548/436 |

FOREIGN PATENT DOCUMENTS

| | | |
|---|---|---|
| 566758 | of 1983 | Australia . |
| 091328A2 | of 1983 | European Pat. Off. . |
| 148440 | of 1984 | European Pat. Off. . |
| 153083 | of 1985 | European Pat. Off. . |
| 162695 | of 1985 | European Pat. Off. . |
| 332968 | of 1989 | European Pat. Off. . |
| 392768 | 10/1990 | European Pat. Off. ... C07D 209/90 |
| 444851 | 9/1991 | European Pat. Off. ... C07D 487/02 |
| 444852 | 9/1991 | European Pat. Off. ... C07D 209/90 |
| 517732 | of 1972 | Fed. Rep. of Germany . |
| 3525564 | of 1985 | Fed. Rep. of Germany . |

OTHER PUBLICATIONS

Flaugh, et al., in J. Med. Chem., 1988, 31, 1746-1753.
Kornfeld, et al., J.A.C.S., 78, 3087 (1956).
Kruse, et al., J. Org. Chem., 49, 4761-4768 (1984).
Bach, et al., J. Med. Chem., 1980, 23, 481-491.
Glennon, J. Med. Chem., 30, 1 (1987).
T. W. Greene, Protective Group in Organic Synthesis, John Wiley and Sons (1981) Chapter 7.
J. W. Barton, Protective Group in Organic Synthesis, McOmie, ed., Plenum Press (1973) Chapter 2.
The Vocabulary of Organic Chemistry, Orchin, et al., John Wiley and Sons, Inc., publishers, p. 126. (1981).
Schoenberg, et al., J. Org. Chem., 39, p. 3327 (1974).
Schoenberg, et al., J. Org. Chem., 39, p. 3318 (1974).
Tetrahedron Letters, 21, 4061 (1980).
Nichols, et al., Org. Prep. & Proc. Int., 9, 277 (1977).
Leanna, et al., Tet. Lett., 30, 3935 (1989).
O. Mitsunobu, Synthesis, Jan. 1981, p. 1.
J. P. Freemer, et al., Synthesis, Dec. 1974, p. 894.
Sugi, et al., Bull Chem. Soc. Jap., 43, p. 1489 (1970).
Morrison & Boyd, Chapter 22, Organic Chemistry, 3rd Ed. (1973).
Wong, et al., J. Neural Transm., 71, 207-218 (1988).
Wong, et al., J. Neural Transm., 64, 251-269 (1985).

Primary Examiner—Mukund J. Shah
Assistant Examiner—Matthew V. Grumbling
Attorney, Agent, or Firm—Douglas J. Taylor; Leroy Whitaker; David E. Boone

[57] ABSTRACT

The present invention provides 4-amino-6-substituted-hexahydrobenz[cd]indoles which are useful in treating disease states which can be benefited by an alteration of 5-HT$_{1A}$ receptors.

15 Claims, No Drawings

6-SUBSTITUTED-HEXAHYDROBENZ[CD]INDOLES

CROSS REFERENCE TO RELATED APPLICATIONS

This application is a continuation of application Ser. No. 07/883,803, filed on May 13, 1992, abandoned, which is a continuation of application Ser. No. 07/567,986 filed on Aug. 15, 1990, abandoned which is a continuation-in-part of commonly assigned and co-pending patent application Ser. No. 07/482,811 filed Feb. 26, 1990 now U.S. Pat. No. 5204,340.

FIELD OF THE INVENTION

This invention relates to the fields of synthetic organic chemistry and pharmaceutical chemistry and involves hexahydrobenz[cd]indoles which are useful in modifying the serotonin function in the body.

BACKGROUND OF THE INVENTION

In recent years it has become apparent that the neuotransmitter serotonin (5-hydroxytryptamine i.e. 5-HT) is associated with a number of physiological phenomena such as acid secretion, anxiety, depression, sexual dysfunction, emesis, memory, hypertension, appetite, and sleep. [Glennon, R. A., *J. Med. Chem.*, 30, 1 (1987)]. Multiple receptors have been found for 5-HT. These receptors have been classified as 5-HT, $5\text{-HT}_1$, and $5\text{-HT}_2$, and $5\text{-HT}_3$ receptors with the former being further classified as $5\text{-HT}_{1A}$, $5\text{-HT}_{1B}$, $5\text{-HT}_{1C}$ and $5\text{-HT}_{1D}$. The binding activity of a compound to one or more of these 5-HT receptors has been recognized as being predictive of physiological activity of the compound.

Flaugh in U.S. Pat. No. 4,576,959 (issued 1986) disclosed a family of 6-substituted-4-dialkylamino-1,3,4,5-tetrahydrobenz[cd]indoles which show binding affinity for 5-HT receptors and are described as central serotonin agonists. Leander in U.S. Pat. No. 4,745,126 (1988) disclosed a method for treating anxiety in humans employing a 4-substituted-1,3,4,5-tetrahydrobenz[cd]indole-6-carboxamide derivative.

Certain indolines have been reported, as in U.S. Pat. No. 4,110,339 of Bach et al. (1978), Flaugh et al., *J. Med. Chem.*, 31, pp 1746-1753 (1988), Flaugh in U.S. Pat. No. 4,576,959 and European Patent Application 0153083 (published 1985). These were used as intermediates in the preparation of the corresponding indoles.

It has now been found that certain 4- and 6-substituted hexahydrobenz[cd]indoles (indolines) particularly certain stereoisomers of such indolines are useful in treating conditions requiring alteration of the $5\text{-HT}_{1A}$ receptor function in the body. The 2aS, 4R isomer has been found to be particularly useful.

SUMMARY OF THE INVENTION

This invention relates to a compound of the Formula IA

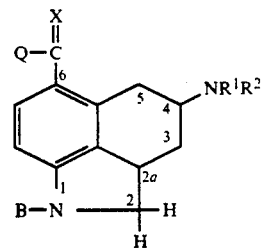

wherein:

$R^1$ is hydrogen, $C_1$-$C_4$ alkyl, $C_3$-$C_4$ alkenyl, phenyl-substituted $C_1$-$C_4$ alkyl, cyclopropylmethyl,

$-(CH_2)_nS(C_1$-$C_4$ alkyl) or $-(CH_2)_n C(O)NR^9R^{10}$;

$R^2$ is hydrogen, $C_1$-$C_4$ alkyl or $C_3$-$C_4$ alkenyl, cyclopropylmethyl;

Q is $OR^3$, $SR^3$, $NR^5R^6$ or hydrogen;

$R^3$ is $C_1$-$C_8$ alkyl, substituted $C_1$-$C_8$ alkyl, aryl, substituted aryl, aryl ($C_1$-$C_4$ alkyl), substituted aryl ($C_1$-$C_4$ alkyl), or $C_3$-$C_7$ cycloalkyl;

$R^4$ is hydrogen, $C_1$-$C_4$ alkyl, $C_1$-$C_4$ haloalkyl, $C_1$-$C_4$ alkoxy or phenyl;

$R^5$ and $R^6$ are independently hydrogen, $C_1$-$C_4$ alkyl, phenyl-substituted $C_1$-$C_4$ alkyl, phenyl, or together form a $C_3$-$C_5$ heterocyclic ring with the proviso that $R^5$ and $R^6$ are not both hydrogen; $R^9$ and $R^{10}$ are independently hydrogen, a $C_1$-$C_4$ alkyl, or a $C_5$-$C_8$ cycloalkyl;

n is 1 to 4;

B is hydrogen, $C_1$-$C_4$ alkyl or an amino-blocking group;

X is oxygen or sulfur; and a pharmaceutically acceptable salt thereof.

This invention further relates to a substantially pure stereoisomer of a compound of the Formula IB

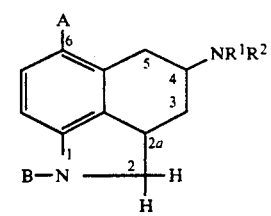

wherein:
A is

hydrogen, halogen, CN, $NO_2$, $NR^5R^6$, $NHC(O)R^6$, $-NHSO_2R^6$, $CONH_2$, $X(C_1$-$C_8$ alkyl), OH, O-acyl, O-benzyl or $CF_3$;

and Q, B, X, $R^1$, $R^2$, $R^3$ $R^5$ and $R^6$ are as defined hereinabove; and positions 2a and 4 have a configuration of S and R respectively; and a pharmaceutically acceptable salt thereof.

The invention also provides a pharmaceutical formulation comprising a compound of Formula IA or IB and a pharmaceutically acceptable excipient therefor.

A further embodiment of the invention is a method for effecting a biological response at the 5-HT$_{1A}$ receptor. More particularly, further embodiments involve treating a variety of conditions which require regulation of serotonin function in the body.

DETAILED DESCRIPTION OF THE INVENTION

As used herein, the term "alkyl" represents a straight or branched alkyl chain having the indicated number of carbon atoms. For example, "C$_1$-C$_4$ alkyl" groups are methyl, ethyl, n-propyl, isopropyl, n-butyl, sec.-butyl, isobutyl and tert-butyl. "C$_1$-C$_8$ alkyl" groups include those listed for C$_1$-C$_4$ alkyl as well as n-pentyl, 2-methylbutyl, 3-methylbutyl, n-hexyl, 4-methylpentyl, n-heptyl, 3-ethylpentyl, 2-methylhexyl, 2,3-dimethylpentyl, n-octyl, 3-propylpentyl, 6-methylheptyl, and the like.

The term "C$_3$-C$_4$ alkenyl" refers to olefinically unsaturated alkyl groups such as —CH$_2$CH=CH$_2$, —CH$_2$CH$_2$CH=CH$_2$, —CH(CH$_3$)CH=CH$_2$ and the like.

The term "aryl" means an aromatic carbocyclic structure. Examples of such ring structures are phenyl, naphthyl, and the like.

The term "cycloalkyl" means an aliphatic carbocyclic structure having the indicated number of carbon atoms in the ring. For example, the term "C$_3$-C$_7$ cycloalkyl" means cyclopropyl, cyclobutyl, cyclopentyl, cyclohexyl, and cycloheptyl.

The term "aryl (C$_1$-C$_4$ alkyl)" means an aromatic carbocyclic structure joined to a C$_1$-C$_4$ alkyl group. Examples of such groups are benzyl, phenylethyl, α-methylbenzyl, 3-phenylpropyl, α-naphthylmethyl, β-naphthylmethyl, 4-phenylbutyl, and the like. Similarly the term "aryl (C$_1$-C$_3$ alkyl)" means an aromatic carbocyclic structure joined to a C$_1$-C$_3$ alkyl.

The C$_1$-C$_8$ alkyl, the aryl, the aryl (C$_1$-C$_4$ alkyl) groups, and aryl (C$_1$-C$_3$ alkyl) can be substituted by one or two moieties. Typical aryl and/or alkyl substituents are C$_1$-C$_3$ alkoxy, halo, hydroxy, C$_1$-C$_3$ thioalkyl, nitro, and the like. Moreover, the aryl, aryl (C$_1$-C$_4$ alkyl) and aryl (C$_1$-C$_3$ alkyl) groups may also be substituted by a C$_1$-C$_3$ alkyl or a trifluoromethyl group.

In the foregoing, the term "C$_1$-C$_3$ alkyl" means any of methyl, ethyl, n-propyl, and isopropyl; the term "C$_1$-C$_3$ alkoxy" means any of methoxy, ethoxy, n-propoxy, and isopropoxy; the term "halo" means any of fluoro, chloro, bromo, and iodo; and the term "C$_1$-C$_3$ thioalkyl" means any of methylthio, ethylthio, n-propylthio, and isopropylthio.

Examples of substituted C$_1$-C$_8$ alkyl are methoxymethyl, trifluoromethyl, 6-chlorohexyl, 2-bromopropyl, 2-ethoxy-4-iodobutyl, 3-hydroxypentyl, methylthiomethyl, and the like.

Examples of substituted aryl are p-bromophenyl, m-iodophenyl, p-tolyl, o-hydroxyphenyl, β-(4-hydroxy)naphthyl, p-(methylthio)phenyl, m-trifluoromethylphenyl, 2-chloro-4-methoxyphenyl, α-(5-chloro)naphthyl, and the like.

Examples of the substituted aryl (C$_1$-C$_4$ alkyl) are p-chlorobenzyl, o-methoxybenzyl, m-(methylthio)-α-methyl-benzyl, 3-(4'-trifluoromethylphenyl)propyl, o-iodobenzyl, p-methylbenzyl, and the like.

The term "C$_3$-C$_5$ heterocyclic ring" includes pyrrolidine, piperidine, morpholine and the like.

The term "amino-blocking group" is used as it is frequently used in synthetic organic chemistry, to refer to a group which will prevent an amino group from participating in a reaction carried out on some other functional group of the molecule, but which can be removed from the amine when it is desired to do so. Such groups are discussed by T. W. Greene in chapter 7 of *Protective Groups in Organic Synthesis*, John Wiley and Sons, New York, 1981, and by J. W. Barton in chapter 2 of *Protective Groups in Organic Chemistry*, J. F. W. McOmie, ed., Plenum Press, New York, 1973, which are incorporated herein by reference in their entirety. Examples of such groups include those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl, benzyl and substituted benzyl such as 3,4-dimethoxybenzyl, o-nitrobenzyl, and triphenylmethyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonylaminocarbonyl. Preferred amino-blocking groups are benzyl (—CH$_2$C$_6$H$_5$), acyl [C(O)R] or SiR$_3$ where R is C$_1$-C$_4$ alkyl, halomethyl 2-halo-substituted (C$_2$-C$_4$ alkoxy), or phenyl.

The compounds of the instant invention have at least 2 chiral centers and therefore at least four stereoisomers can exist for each. If a substituent group contains a chiral center, then additional stereoisomers can of course exist. The racemic mixtures of the compounds of Formula IA as well as the substantially pure stereoisomers of Formula IB are contemplated as within the scope of the present invention. The term "substantially pure" refers to at least about 90 mole percent, more preferably 95 mole percent and most preferably at least 98 mole percent of the desired stereoisomer being present compared to the other stereoisomers present. Particularly preferred stereoisomers are those in which the configuration of the chiral centers at position 2a is S and at position 4 is R.

The terms "R" and "S" are used herein as commonly used in organic chemistry to denote specific configuration of chiral center. The term "R" refers to "right" and refers that configuration of a chiral center with a clockwise relationship of group priorities (highest to second lowest) when viewed along the bond toward the lowest priority group. The term "S" or "left" refers to that configuration of a chiral center with a counterclockwise relationship of group priorities (highest to second lowest) when viewed along the bond toward the lowest priority group. The priority of groups is based upon their atomic number (heaviest isotope first). A partial list of priorities and a discussion of stereo chemistry is contained in the book: *The Vocabulary of Organic Chemistry*, Orchin, et al. John Wiley and Sons Inc., publishers, page 126, which is incorporated herein by reference.

While all of the compounds of the invention are useful for the purposes taught herein, certain of the present compounds are preferred for such uses. Preferably X is oxygen or sulfur; R$^1$ is hydrogen, C$_1$-C$_4$ alkyl, allyl or C(O)R$^4$; R$^2$ is hydrogen, C$_1$-C$_4$ alkyl, or allyl; R$^3$ is C$_1$-C$_4$ alkyl; R$^4$ is hydrogen, methyl, ethyl, propyl, trifluoromethyl or phenyl; and $R^5$ and $R^6$ are independently hydrogen, a $C_1$–$C_4$ alkyl, a phenyl ($C_1$–$C_4$ alkyl), phenyl or together form a $C_3$–$C_5$ heterocyclic ring with the proviso that $R^5$ and $R^6$ are not both hydrogen. More preferably X is oxygen, $R^1$ and $R^2$ are both $C_1$–$C_4$ alkyl, and especially n-propyl, and $R^3$ is hydrogen or $C_1$–$C_3$ alkoxy particularly methoxy or ethoxy. Other preferred aspects of the present invention are noted hereinafter.

As set forth above, this invention includes the pharmaceutically-acceptable salts of the compounds of Formula IA and IB. Since the compounds of this invention are basic in nature and accordingly they react with any number of inorganic and organic acids to form pharmaceutically acceptable salts such as hydrochloric acid, nitric acid, phosphoric acid, sulfuric acid, hydrobromic acid, hydroiodic acid, phosphorous acid and others, as well as salts derived from non-toxic organic acids such as aliphatic mono and dicarboxylic acids, amino acids, phenyl-substituted alkanoic acids, hydroxyalkanoic and hydroxyalkandioic acid, aromatic acids, aliphatic and aromatic sulfonic acids. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, tartrate isobutyrate, caprate, heptanoate, propiolate, oxalate, malonate, succinate, suberate, sebacate, fumarate, maleate, mandelate, butyne-1,4-dioate, hexyne-1,6-dioate, hippurate, benzoate, chlorobenzoate, methylbenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, naphthalene-1sulfonate, naphthalene-2-sulfonate and mesylate.

The following list illustrates representative compounds of the present invention:

4-(dimethylamino)-1,2,2a,3,4,5-hexahydrobenz[c,d]indole-6-carbothioic acid, S-methyl ester;
4-(di-n-propylamino)-1,2,2a,3,4,5-hexahydrobenz[c,d]indole-6-carbothioic acid, O-ethyl ester;
4-(methylethylamino)-1,2,2a,3,4,5-hexahydrobenz[c,d]indole-6-carbodithioic acid, methyl ester;
4-(n-butylamino)-1,2,2a,3,4,5-hexahydrobenz[c,d]indole-6-carboxylic acid, ethyl ester;
4-(di-n-propylamino)-1,2,2a,3,4,5-hexahydrobenz[c,d]indole-6-carbothioic acid, S-methyl ester;
4-amino-1,2,2a,3,4,5-hexahydrobenz[c,d]indole-6-carbodithioic acid, n-propyl ester;
4-(methylamino)-1,2,2a,3,4,5-hexahydrobenz[c,d]indole-6-carboxylic acid, n-propyl ester;
4-amino-1,2,2a,3,4,5-hexahydrobenz[c,d]indole-6-carboxylic acid, methyl ester;
4-(diethylamino)-1,2,2a,3,4,5-hexahydrobenz[c,d]indole-6-carboxylic acid, n-propyl ester maleate;
(2aS,4R)-4-(di-n-propylamino)-6-iodo-1,2,2a,3,4,5-hexahydrobenz[cd]indole;
4-(dimethylamino)-1,2,2a,3,4,5-hexahydrobenz[c,d]indole-6-carboxylic acid, methyl ester;
4-(di-n-propylamino)-1,2,2a,3,4,5-hexahydrobenz[c,d]indole-6-carboxaldehyde;
4-(methylethylamino)-1,2,2a,3,4,5-hexahydrobenz[c,d]indole-6-carboxylic acid, ethyl ester;
4-(di-n-propylamino)-6-aminocarbonyl-1,2,2a,-3,4,5-hexahydrobenz[c,d]indole;
(2aS, 4R)-4-(di-n-propylamino)-6-aminocarbonyl-1,2,2a,3,4,5-hexahydrobenz[c,d]indole;
(2aS,4R)-4-(di-n-propylamino)-6-bromo-1,2,2a,-3,4,5-hexahydrobenz[c,d]indole;
(2aS,4R)-4-(di-n-propylamino)-6-cyano-1,2,2a,-3,4,5-hexahydrobenz[c,d]indole; and
(2aS,4R)-4-(di-n-propylamino)-6-methoxy-1,2,-2a,3,4,5-hexahydrobenz[c,d]indole.

In a preferred method of preparation, 6-iodo-1,2,2a,3,4,5-hexahydrobenz[cd]indole 2 is a useful intermediate to the instant compounds in which the substituent at the 6-position is aminocarbonyl, alkyl- or aryl-substituted amides, or alkyl-or aryl-carboxylic acid esters. The aminocarbonyl group can be introduced by reacting the 6-iodo indoline with ammonia and carbon monoxide in the presence of a palladium catalyst as described by Schoenberg et al. *J. Org. Chem.*, 39, p 3327, 1974 and Schoenberg et al. *J. Org. Chem.*, 39, p 3318, 1974 (both incorporated herein by reference). Substituted amides can be introduced at the 6-position by using an amine instead of ammonia in the reaction. Carboxylic acid esters substituted at the 6-position can be prepared by using alcohols in place of ammonia. The preferred palladium catalysts are bis(triphenylphosphine)palladium chloride, bis(triphenylphosphine)palladium bromide and tetrakis(triphenylphosphine)palladium. Inert solvents such as acetonitrile or toluene are suitable. When ammonia is used, an approximately equimolar mixture of carbon monoxide and ammonia is supplied to the reaction at approximately one to approximately twenty atmospheres of pressure. When a reactant such as an amine or an alcohol is used in place of ammonia, the reagents are mixed in a reaction vessel and the desired pressure of carbon monoxide is introduced. The reaction mixture is stirred at a temperature between about 25° C. and about 150° C. until the 6-iodo indoline is substantially consumed, as determined, for example, by thin layer chromatography or liquid chromatography. This reaction can then be followed by additional steps to remove any amino-protecting groups and add alkyl, alkenyl, or other desired substituents to the amino group at the 4-position. Of course, modifications to this synthetic route may be desirable.

Preferably the 1-nitrogen is blocked with a protecting group Z such as a tert-butoxycarbonyl group before the carbonylation is initiated. Compounds that contain reactive 6-substituents should also contain a relatively labile 1-amino protecting group in order for the protecting group to be selectively removed. For example, when 6-alkoxycarbonyl derivatives are prepared, it may be preferred to use a 1-amino protective group such as the Cl$_3$CCH$_2$OCO— moiety instead of tert-butoxycarbonyl and particularly instead of a benzoyl group. Depending upon the desired final product, the 4-amino group can be protected with a readily removable blocking group such as benzoyl when $R^1$ and/or $R^2$ is hydrogen. Amino blocking groups including acyl groups such as formyl, acetyl, trifluoroacetyl and the like can be introduced at the 4-amino position using methods disclosed by T. W. Greene in Chapter 7 of *Protective Groups in Organic Synthesis*, John Wiley and Sons, New York, 1981, and by J. W. Barton in Chapter 2 of Protective Groups in Organic Chemistry, J. F. W. McOmie, ed., Plenum Press, New York, 1973. When $R^1$ or $R^2$ is alkyl or alkenyl in the desired compound of Formula I, it is preferred that the 4-amino group be alkylated before the carbonylation is accomplished.

In another method of preparation the 6-ester and 6-amide compounds of formula IA can be prepared from the 6-carboxylic acid derivative. For example, the 6-carboxylic acid can be reacted with a reagent RQH (where R is of the desired carbon-containing substituent and Q is oxygen or nitrogen) and a coupling reagent. Any of type of the coupling reagents commonly employed in the synthesis of peptides can be used and the desired ester or amide isolated. Examples of such coupling reagents include carbodiimides, such as N,N'-dicyclohexylcarbodiimide, N,N'-diisopropylcarbodiimide or N,N'-diethylcarbodiimide; the imidazoles such as carbonyl diimidazole as well as reagents such as N-ethoxycarbonyl-2-ethoxy-1,2-dihydroquinoline.

An alternative method of preparation is depicted in Scheme I in which $R^1$ and $R^2$ are as defined above and Z is an appropriate amino-blocking group. The 1-nitrogen of the 6-bromo compound 3 is protected with an appropriate blocking group which should be relatively nonreactive to butyllithium. A preferred blocking group is the benzyl group which can be affixed to the 1-nitrogen by the reaction of compound 3 with benzyl chloride. The 1-benzyl-6-bromo derivative 4 is contacted with a lithiating reagent such as n-butyllithium or t-butyllithium. The reagents are combined at a temperature in the range of about $-100°$ C. to about $-20°$ C. more preferably about $-60°$ C. to about $-40°$ C. The 6lithium derivative 5 can then be converted to the 1,6-disubstituted-4-aminohexahydrobenz-[c,d]indole 6 upon reaction with an appropriate electrophile such as $R^3C(=X)Y$, wherein X is defined above and Y is a good leaving group such as cyano. Typically a solution of the compound 5 at a temperature in the range of about $-100°$ C. to about $-60°$ C., preferably at about $-80°$ C., is added to a solution of the electrophile in a mutual solvent. The desired compound 6 is purified by quenching the reaction mixture with, for example, ice water. The mixture is washed with a water-immiscible organic solvent. The organic phase is extracted with acid, and the aqueous phases are combined, made basic and the desired compound extracted with a water immiscible organic solvent. The organic solvent is removed, typically under vacuum, and the desired compound 6 is further purified if necessary by standard procedures. A disadvantage of this procedure is that some dehalogenation may occur resulting in a hydrogen in the 6-position which can require additional purification steps to obtain substantially pure compound 6.

Scheme I

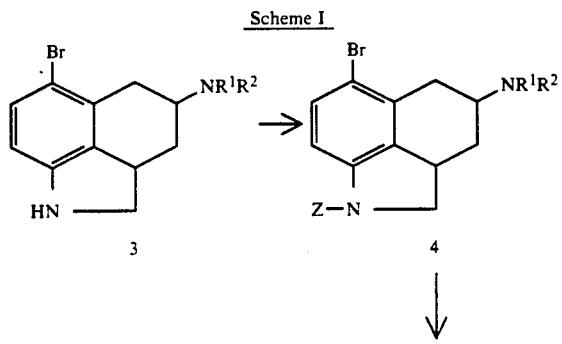

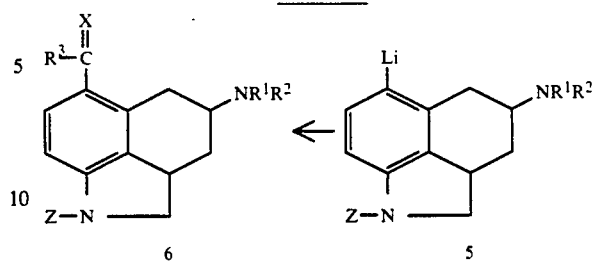

The 6-lithium derivative 5 can be used to prepare the corresponding 6-carboxylic acid derivative by contacting the 6-lithium derivative with carbon dioxide. The 6-carboxylic acid can be used as an intermediate to prepare the 6-amides and 6-esters of the instant invention by standard amidation and esterification methods.

Thiocarboxylic acid esters defined by Formula IA wherein X is sulfur, form another important group of compounds that are a further embodiment of this invention. The thiocarboxylic acid esters of the invention can be prepared by thiating the corresponding carboxylic acid ester or thioester. Any of several thiating agents can be employed in this reaction including phosphorous pentasulfide. Another thiating agent is Lawesson's Reagent, which is 2,4-bis(4-methoxyphenyl)-1,3-dithia-2,4-diphosphetane-2,4-disulfide. This thiating agent and its general uses are described in detail in *Tetrahedron Letters*, 21, 4061 (1980). The thiation reation is preferably carried out by combining approximately equimolar quantities of the carboxylic acid ester and thiating agent in a mutual organic solvent such as toluene or dioxane. The reaction is generally complete within about 1 hour to about 10 hours when carried out at a temperature of about 50° C. to about 150° C. The thiocarboxylic acid esters thus formed can be isolated and purified by normal methods such as crystallization and the like.

The compounds of Formula IA where X is sulfur can also be prepared by reacting the 4-amino-6-lithiumtetrahydrobenz[c,d]indole 5, prepared as described above, (or the corresponding Grignard reagent) sequentially with carbon disulfide and a suitable electrophile or with thiocarbonyl-1,1'-diimidazole and a suitable nucleophile.

Compounds of Formula IB in which A is $-NR^5R^6$, i.e. 6-amino and substituted 6-amino compounds, can be prepared from the corresponding 6-nitro indoline. The nitro is reduced to the corresponding 6-amine using common reducing agents such aluminum hydride. The resulting amine can then be alkylated with the desired groups using methods well known to those skilled in the arts, such as contacting the amine with an alkyl halide in the presence of sodium carbonate or contacting the amine with an alcohol in the presence of a catalytic amount of aluminum t-butoxide and Raney Nickel.

Compounds of Formula IB in which A is $O(C_1-C_4$ alkyl) or $S(C_1-C_4$ alkyl) can be prepared from the corresponding 6-bromoindoline by displacement with the appropriate alkoxide or thioalkoxide in the presence of cuprous iodide. For example, the 6-methoxy derivative can be prepared by contacting the 6-bromo indoline with sodium methoxide in the presence of CuI.

Compounds of Formula IB in which A is OH can be prepared by ether cleavage of a corresponding 6-alkoxyindoline. This ether cleavage can be effected by using standard reagents such as boron tribromide or boron trichloride.

The 6-hydroxyindoline can be used as an intermediate in the preparation of the corresponding O-acyl or O-benzyl compounds of Formula IB. These O-acyl compounds can be prepared using standard acylation reactions with the 6-hydroxy indoline. For example, the appropriate acyl chloride or appropriate anhydride can be contacted with the 6-hydroxyindoline. The O-benzyl compounds can be prepared by contacting the appropriate 6-hydroxindoline with a benzylhalide.

The compounds of Formula IB in which A is $CF_3$ can be prepared by contacting the corresponding 6-carboxylic acid with $SF_4$. Alternatively, these compounds can be prepared by heating a mixture of the corresponding 6-bromo compounds, CuI, $CF_3CO_2Na$, and N-methyl-2-pyrrolidone at 100° to 180° C.

Scheme 2 illustrates the preparation of intermediates useful in preparing the compounds of the instant invention. As is readily apparent, when compounds of structure 7 are available in which A is the desired 6-substituent, the desired compounds of Formula 1B can be prepared directly. However, the preferred route is to use the readily available starting ketone of formula 7 in which A is hydrogen and B is a benzoyl group.

Epoxides of formula 8 are known in the art or can be prepared from compounds known to the art using common reagents and techniques. For example, Flaugh, et al., *J. Med. Chem.*, 31, 1746 (1988); Nichols et al., *Org. Prep. and Proc., Int.*, 9, 277 (1977); and Leanna et al., *Tet. Lett.*, 30, No. 30, 3935 (1989), teach methods of preparation of various embodiments of compounds of formula 8. Those skilled in the art of organic chemistry will recognize that there are four stereoisomers of formula 8:

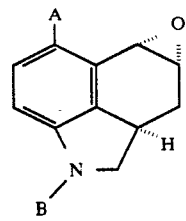
8a

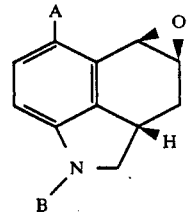
8b

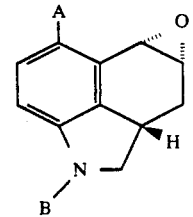
8c

8d

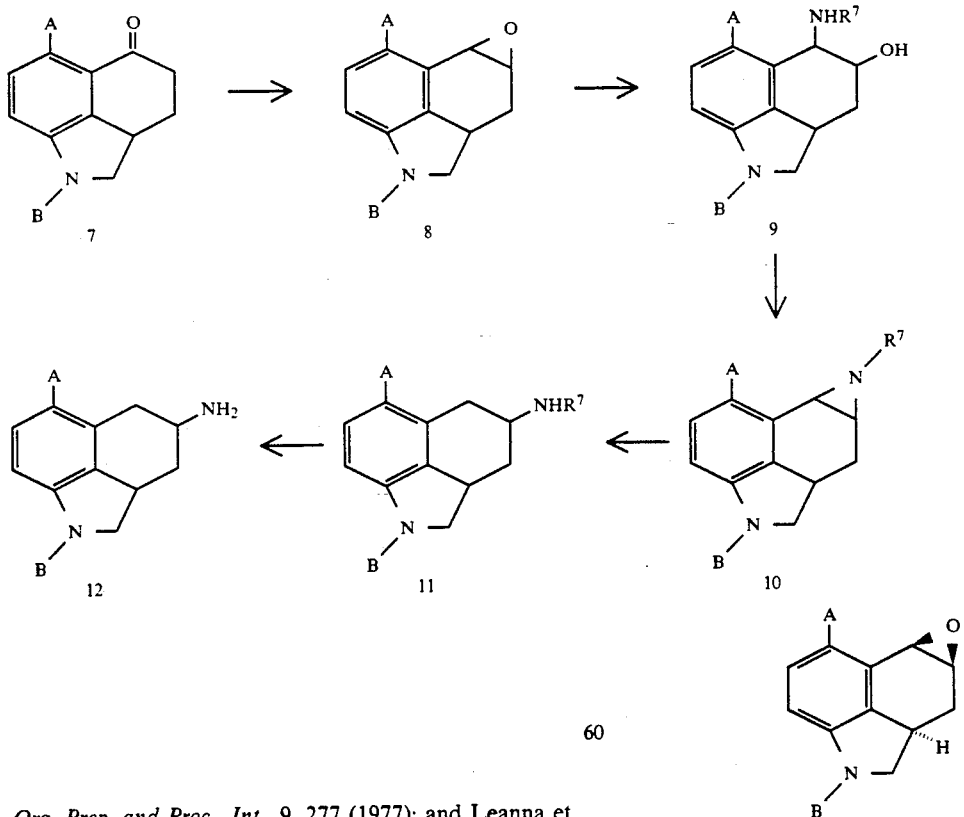

formulae $8_a$ and $8_b$ are herein referred to collectively as the exo-isomers; similarly, formulae $8_c$ and $8_d$ are the endo-isomers. Leanna et al., supra, teach the preparation of epoxides of formula 8 which are substantially exo or substantially endo, as desired. The preferred starting material is the compound of formula 8 wherein B is benzoyl and A is hydrogen with the most preferred starting material being a mixture of the exo-isomers thereof.

Amino alcohols of formula 9 are formed by reacting an epoxide of formula 9 with an amine of formula $R^7NH_2$. Such amines are readily available. Opening of the epoxide ring proceeds substantially regiospecifically with the amino group at the 5-position and the hydroxyl group at the 4-position. The reaction is also stereospecific in the sense that stereoisomers of formulae $9_{a-d}$ are predictably formed from, respectively, stereoisomers of formulae $8_{a-d}$.

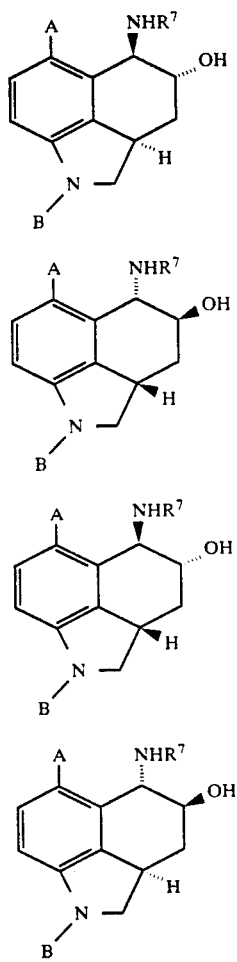

A stereoselective synthesis of the amino alcohol of formula 9, and hence of all the subsequent intermediates and products of Scheme 2, can be effected by using a substantially pure enantiomer of an amine of the formula $R^7NH_2$ wherein $R^7$ contains at least one chiral center. The diastereomers of the resulting amino alcohol can then be separated by a number of means known in the art, for example by chromatography or crystallization. Suitable solvents for recrystallization include those such as diethyl ether, n-butanol, and mixtures of hexane and ethyl acetate. An alternative method of achieving a stereospecific synthesis comprises conversion of all the diastereomers of formula 9 to corresponding diastereomers of formula 10, followed by the separation of the diastereomers that alternative method is discussed below. If a stereoselective synthesis is not desired, then no separation of the stereoisomers of the amino alcohol of formula 8 is required and the amine $R^7NH_2$ need not be optically active. In this case, $R^7$ could be the same as $R^1$ and formula 11 could be used to prepare the desired compound.

A particularly efficient stereoselective process for a highly preferred compound of formula 9, 1-benzoyl-4-hydroxy-5-(1-phenylethyl)amino-1,2,2a,3,4,5-hexahydrobenz[cd]indole, comprises the reaction of a mixture of substantially the exo-isomers of the corresponding epoxide of formula 8, or a mixture of substantially the endo-isomers of the corresponding epoxide of formula 8, with a substantially pure enantiomer of 1-phenethylamine in a suitable solvent such as n-butanol and the subsequent selective crystallization of one of the two isomers of the amino alcohol. The temperature of the reaction can be from about 50° to about 150° C., preferably about 80° to about 100° C.

After the reaction is complete, as determined for example by thin layer chromatography or liquid chromatography, the desired amino alcohol is crystallized at about −20° to about 40° C. with the preferred temperature being between about 0° and 15° C. This process has the valuable attribute that the reaction and the separation of stereoisomers occur efficiently in a single step. By the proper selection of the epoxide isomers, exo or endo, and the enantiomer of 1-phenylethylamine, R or S, one can determine which of the stereoisomers of the compound of formula 9 precipitates from the reaction mixture. For example, a preferred stereoisomer of 1-benzoyl-4-hydroxy-5-(1-phenylethyl)amino-1,2,2a,3,4,5-hexahydrobenz[cd]indole, the (2a-S,4-S,5-S)-isomer (structure 9b), can be selectively prepared by reacting the exo-epoxides with S-1-phenylethylamine.

A number of methods of forming aziridines such as those of formula 10 from amino alcohols such as those of formula 9 are known to the art. Two examples are the use of diethyl azodicarboxylate and triphenylphosphine (O. Mitsunobu, Synthesis, January, 1981, page 1), and the use of bromine and triphenylphosphine (J. P. Freemer and P. J. Mondron, Synthesis, December, 1974, page 894).

A particularly efficient alternative to the above methods involving treating a compound of formula 9 with a tertiary amine in an inert solvent followed by the addition of methanesulfonyl chloride. The following stereoisomers of the aziridine of formula 10, $10_{a-d}$ arise respectively from the stereoisomers of formula $9_{a-d}$ with retention of configuration at any chiral center in the substituents A, B or $R^7$ as well as at position 2a:

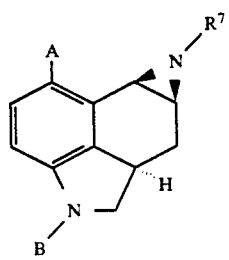

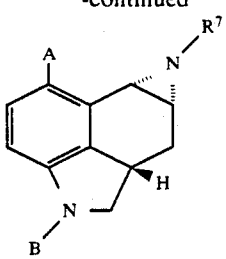

10b

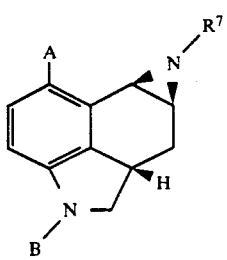

10c

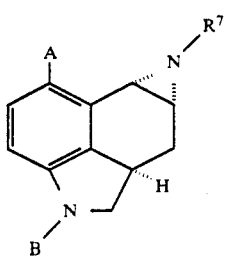

10d

Suitable tertiary amines are those of the formula $(R^8)_3N$, where the $R^8$ groups are independently $C_1$–$C_4$ alkyl. Suitable solvents are chlorinated hydrocarbons such as methylene chloride, chloroform, carbon tetrachloride, and dichloroethane; aromatic hydrocarbons such as benzene, toluene, and the xylenes; and ethers such as tetrahydrofuran, diethyl ether, and methyl t-butyl ether. The reaction can be conducted at a temperature from about −35° to about 45° C. In a preferred embodiment, the amino alcohol is treated with triethylamine in methylene chloride at about −20° to about 0° C., then the reaction mixture is warmed to about 15° to about 35° C. for the completion of the reaction. If desired, the product, an aziridine of formula 10, can be crystallized from an appropriate solvent such as acetonitrile or isopropanol after an aqueous workup. In the event that $R^7$ contains at least one chiral center in substantially a single stereoconfiguration and that the aziridine of formula 10 is prepared as a mixture of stereoisomers, said stereoisomers can be separated by methods such as chromatography and crystallization, thereby providing a stereospecific synthesis of the aziridine of formula 10 and subsequent products.

The aziridine ring can be opened to form an intermediate secondary amine of formula 11. A number of methods of opening aziridines are commonly known. It is, however, crucial that the method used for opening the aziridine to form a secondary amine of formula 11 be substantially regiospecific; the aziridine must be opened to form substantially the 4-amino compound rather than the 5-amino compound. One such method is catalytic hydrogenolysis as taught by Y. Sugi and S. Mitsui, *Bull. Chem. Soc. Jap.*, 43, pp. 1489–1496 (1970). Catalysts which are suitable are the usual hydrogenation and hydrogenolysis catalysts, such as the noble metal catalysts; the preferred catalyst is palladium. Suitable solvents include hydrocarbons such as hexanes and heptanes; aromatic hydrocarbons such as benzene, toluene, xylenes, ethylbenzene, and t-butylbenzene; alcohols such as methanol, ethanol, and isopropanol; and mixtures of solvents such as acetic acid mixed with said alcohols. Preferred solvents for preparing the compound of formula 11, wherein B is benzoyl, A is hydrogen, and $R^7$ is 1-phenylethyl, include glacial acetic acid or a mixture of methanol and phosphoric acid. The source of hydrogen can be an atmosphere of hydrogen supplied at a pressure of about 1 atmosphere or higher, or the source of hydrogen can be compounds which are suitable to serve as hydrogen donors in a catalytic transfer hydrogenolysis reaction, such as formic acid, cyclohexene, or hydrazine. The preferred hydrogen source is an atmosphere of hydrogen gas supplied at about 1 to about 10 atmospheres pressure. The temperature of the reaction may be from about −20° to about 80° C.; the preferred temperature for the hydrogenolysis of the aziridine wherein B is benzoyl, A is hydrogen, and $R^7$ is 1-phenylethyl is about −20° to about 0° C.

The conversion of compounds of formula 10 to compounds of formula 11 proceeds without disturbing the stereochemical configuration of the chiral centers at the 2a- or 4- positions of the formula 11 or of the chiral centers that may be present in any of the substituents.

If desired, the compound of formula 11 can be isolated by the usual methods such as crystallization. The secondary amine of formula 11 can be converted to a primary amine of formula 12 by a number of methods known to the art of organic chemistry, or alternatively the secondary amine itself can be isolated. However, a preferred method is to convert the secondary amine of formula 11 to the primary amine of formula 12 without isolating the secondary amine, but rather by simply continuing, without interruption, the hydrogenolysis reaction that produced the compound of formula 11. Therefore, the preferred solvent and catalyst are the same as those for the preparation of the secondary amine of formula 11. It may be desirable to conduct the hydrogenolysis of the secondary amine of formula 11 at a different temperature or a different pressure or different temperature and pressure than the hydrogenolysis of the aziridine of formula 10. For the hydrogenolysis of the preferred compound of formula 11 wherein B is benzoyl, A is hydrogen, and $R^7$ is 1-phenylethyl, the preferred temperature and pressure are about 50° to about 60° C. and about 1 to about 20 atmospheres.

The hydrogenolysis of compounds of formula 11 to compounds of formula 12 proceeds without disturbing the stereochemical configuration of the chiral centers at the 2a- or 4- positions.

The isolation of the compound of formula 12 can be accomplished by the usual methods such as crystallization. If desired, the compound of formula 12 can be further purified, for example by recrystallization.

Of course, as those skilled in the art will recognize, variations of Scheme 2 may be desirable or necessary for certain embodiments of the invention. For example, it may be undesirable to subject a compound in which A is halo to the catalytic hydrogenolysis steps of Scheme 2 because the undesired displacement of the halogen may compete with the desired hydrogenolysis of the carbon-nitrogen bonds. Typically it is preferred to postpone the halogenation until after the hydrogenolysis. Another alternative strategy is to use a milder means of reduction that would leave the halogen in place. A third alternative is to perform the desired displacement of halogen before the hydrogenolysis step although care must be exercised if the new group at the 6-position is sensitive to hydrogenation.

Compounds of Formula I can be prepared from the compounds of formula 12, whether they exist as a mixture of stereoisomers or as substantially pure enantiomers, using common reagents and methods well known in the art. The 6-bromo indoline is a preferred intermediate in the preparation of many of the compounds of Formulae IA and IB. The 6-bromo derivative can be prepared by standard phenyl bromination reactions such as with bromine in acetic acid or with N-bromosuccinimide.

In addition to the 6-bromo derivative, another preferred intermediate to the compounds of the instant invention is the 6-iodo derivative 2 as discussed hereinabove. Preferably B is an amino-blocking group such as benzoyl or p-nitrophenylethyl. A preferred method of introducing iodine at the 6-position is by reaction of the 6-hydro indoline with iodine and orthoperiodic acid in the presence of an acid such as trifluoroacetic acid or sulfuric acid, in a solvent such as acetic acid. Another preferred method of iodination is by the use of N-iodosuccinimide in the presence of trifluoroacetic acid. Amino blocking groups can be added, if desired, to the 4-amino substituent using such methods as those disclosed by Greene, supra, and Barton, supra. Alkyl groups can be added, if desired, to the 4-amino substituent using such common methods as reaction with of the appropriate halide as discussed on pages 734 and 735 of Morrison and Boyd, Chapter 22, *Organic Chemistry*, Third Edition, Allyn and Bacon, Boston, 1973.

A particularly preferred intermediate is (2a-S,4-R)-1-benzoyl-4-(di-n-propyl)amino-6-iodo-1,2,-2a,3,4,5-hexahydrobenz[cd]indole, formula 13.

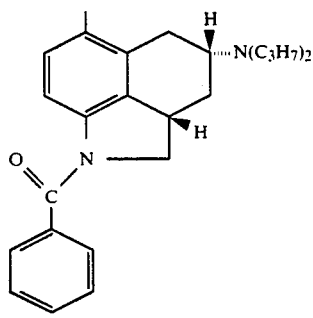

13

This can be prepared from the compound of formula 12 where B is benzoyl and A is hydrogen by iodination as described above followed by alkylation of the 4-amino group with n-propyl iodide in the presence of a base such as potassium carbonate in a solvent such as acetonitrile.

The 6-nitrile indoline can be prepared from the corresponding 6-bromo derivative by contacting the bromo compound with cuprous cyanide at an elevated temperature such as 200° C. Other known methods can be used such as contacting the 6-bromo indoline with sodium cyanide in the presence of alumina.

The 6-nitrile indoline compounds can be hydrolyzed by known methods such as aqueous acid or base at elevated temperatures to provide the 6-carboxylic acid derivative. Hydrolysis of the 6-nitrile with polyphosphoric acid can conveniently provide the 6-carboxamide derivative.

The 6-nitro derivatives can be prepared from compounds of formula 12 by nitration using standard methods such as a mixture sulfuric acid and nitric acid. The nitro group can be reduced, for example by catalytic hydrogenation, to provide the 6-amino derivative. The 6-amino indoline can be alkylated to provide 6-substituted-amino indolines.

The following examples further illustrate the preparation of compounds of this invention. The examples are provided for purposes of illustration only and are not to be construed as limiting the scope of the instant invention in any way.

The terms and abbreviations used in the instant examples have their normal meaning unless otherwise designated, for example, "°C." refers to degrees celsius; "N" refers to normal or normality; "mmole" refers to millimole; "g" refers to gram; "ml" means milliliter; "M" refers to molar; "NMR" refers to nuclear magnetic resonance; "IR" refers to infrared spectroscopy; "U.V." refers to ultraviolet spectroseopy; and "m.s." refers to mass spectrometry.

EXAMPLE 1

Preparation of (2aR,4S)-1-benzoyl-4-amino-6-bromo-1,2,2a,3,4,5-hexahydrobenz[cd]indole (2aR,4S)-1-Benzoyl-4-amino-1,2,2a,3,4,5-hexahydrobenz[cd]indole (29.4 g, 0.106 mole) was placed into a 500 ml three neck round bottom flask equipped with a mechanical stirrer, a nitrogen inlet and a constant addition funnel. The substrate was dissolved in glacial acetic acid (250 ml), and sodium acetate (34.7 g, 0.423 mole, 4 mol equiv) was then added. A solution of bromine (21.8 ml, 0.424 mole) in acetic acid was then added dropwise over a period of one hour with vigorous stirring and then stirred at room temperature overnight. The resulting thick slurry was diluted with ethyl ether, filtered and washed with ethyl ether. The material thus obtained was slurried in H$_2$O and the pH adjusted to 11-12 with 5N NaOH. The solid was filtered, washed well with H$_2$O and dried in vacuo to provide 33.6 g (88.8%) of the title compound. An analytical sample was prepared by recrystallization from isopropyl alcohol. m.p.: 169°–173° C.

IR: 3010, 2934, 1640, 1580, 1468, 1454, 1384 cm$^{-1}$.

NMR: ($^1$H, ppm, CDCl$_3$): 7.42–7.58 (m, 7H), 4.27 (br s, 1H), 3.68 (t, 1H, j=11.1 Hz), 3.33 (m, 2H), 3.16 (dd, 1H, J=6.3, 17.3 Hz), 2.28 (dd, 1H, J=9.6, 17.3 Hz), 2.17 (m, 1H), 1.44 (br s, 2H), 1.32 (q, 1H, J=11.6 Hz). ($^{13}$C, ppm, CD$_3$OD): 170.6, 141.9, 137.3, 136.4, 134.1, 132.1, 132.0, 129.8, 128.1, 118.8, 116.2, 59.5, 49.3, 37.8, 37.1, 25.4.

M.S.: m/e=356, 358, 339, 341, 105, 77.

U.V.: $\lambda_{max}$=272 ($\epsilon$=14400) in ethanol.

Analysis: Theory: C, 60.52; H, 4.80; N, 7.82; Found: C, 60.33; H, 4.89; N, 7.72.

[$\alpha$]$_D$= +20.73 (589 nm).

EXAMPLE 2

Preparation of (2aS, 4R)-1-benzoyl-4-amino-6-bromo-1,2,2a,3,4,5-hexahydrobenz[c,d]indole The procedure of Example 1 was followed using (2aS, 4R)-1-benzoyl-4-amino-1,2,2a,3,4,5-hexahydrobenz[c,d]indole to provide the named compound.

EXAMPLE 3

Preparation of (2aR, 4S)-1-Benzoyl-4-(di-n-propyl)amino-6-bromo-1,2,2a,3,4,5-hexahydrobenz[cd]indole (2aR, 4S)-1-Benzoyl-4-amino-6-bromo-1,2,2a,3,-4,5-hexahydrobenz[cd]indole (9.82 g, 0.0275 mol) was placed in 500 ml round bottom flask equipped with a mechanical stirrer, condenser topped with a nitrogen inlet, and a thermocouple. Acetonitrile (175 ml) and $K_2CO_3$ (0.275 mol) were added, followed by the addition of propyl iodide (13.2 ml, 0.137 mol) with vigorous stirring. The reaction mixture was stirred at 75°±5° C. under nitrogen overnight. After cooling to room temperature, the reaction mixture was diluted with $CH_2Cl_2$ (200 ml) and washed successively with $H_2O$, $NaHCO_3$ solution, $H_2O$, brine and dried over $Na_2SO_4$. After filtration, the volatiles were removed in vacuo to provide 11.5 g (94%) crude product. This material was then recrystallized from 95% ethanol to provide the desired product as colorless needles 9.7 g (80.0%).

m.p.: 93°-93° C.
IR: 2958, 1655, 1464, 1453, 1381 cm$^{-1}$.
NMR: ($^1$H, ppm, CDCl$_3$): 7.41–7.58 (m, 7H), 4.27 (m, 1H), 3.34 (m, 1H), 3.19 (m, 1H), 2.92 (dd, 1H, J=5.6, 18.1 Hz), 2.48 (m, 5H), 2.16 (m, 1H), 1.47 (m, 4H), 1.40 (m, 1H), 0.90 (t, 6H, J=7.3 Hz). ($^{13}$C, ppm, CDCl$_3$): 168.9, 140.9, 134.7, 131.3, 130.0, 128.9, 127.7, 118.6, 57.8, 53.1, 30.6, 29.2, 22.9, 12.1.
M.S: m/e=440/442.
U.V.: $\lambda_{max}$=272 ($\epsilon$=15600) in ethanol.
Analysis: Theory: C, 65.31; H. 6.62; N, 6.35; Br, 18.10 Found: C, 65.15; H, 6.70; N, 6.36; Br, 18.31.
$[\alpha]_{589}$=11.6° (ethanol).

EXAMPLE 4

Preparation of (2aS, 4R)-1-benzoyl-4-(di-n-propyl)amino-6-bromo-1,2,2a,3,4,5-hexahydrobenz[c,d]indole The same procedure as in Example 3 was followed using (2aS, 4R)-1-benzoyl-amino-6-bromo-1,2,2a,3,4,5-hexahydrobenz[c,d]indole to provide the novel compound.

EXAMPLE 5

Preparation of (2aR,4S)-1-benzoyl-4-(di-n-propyl)amino-6-cyano-1,2,2a,3,4,5-hexahydrobenz[cd]indole A. (2aR,4S)-1-Benzoyl-4-(di-n-propyl)amino-6-bromo-1,2,2a,3,4,5-hexahydrobenz[cd]indole (154.48 g, 0.35 mol) was dissolved in N-methylpyrrolidinone (NMP, 850 ml) to which CuCN (37.6 g, 0.42 mol, 1.2 mole equiv) was added. The flask was equipped with a condenser topped with a Firestone valve, a thermocouple, and a mechanical stirrer. The mixture was degassed five times (vacuum/N$_2$ purge via Firestone valve) and slowly brought to 200° C.±5° C. (internal temp). After 1 hour, TLC indicated that the reaction was nearly complete. After a total of 2.5 hours, TLC showed no starting material present. The resulting dark reaction mixture had precipitated Cu on the flask walls, and was then cooled to room temperature. The mixture was diluted with CH$_2$Cl$_2$ (1 1) and washed with 15% NH$_4$OH (=500 ml water+500 ml concentrated reagent). The layers were separated and the aqueous phase was extracted with CH$_2$Cl$_2$ (500 ml). The combined organic layers were washed with H$_2$O (4×1 L), brine (1 L) and dried over Na$_2$SO$_4$. The dessicant was removed by filtration, and the filtrate concentrated to dryness. The crude residue was chromatographed in several small portions over silica gel with a hexane/ethyl acetate gradient to provide 102.7 g of the nitrile (75.7%). This material was used in the subsequent deprotection step without crystallization. A portion of this material was recrystallized from 50% aqueous ethanol for analysis.

m.p.: 109°-111° C.
IR: 2959, 2213, 1661, 1616, 1470, 1453, 1368, 1355 cm$^{-1}$.
NMR: ($^1$H, ppm, CDCl$_3$): 7.34–7.58 (m, 7H), 4.35 (m, 1H), 3.72 (t, 1H, J - 11.2 Hz), 3.30 (m, 2H), 3.13 (m, 1H), 2.72 (m, 1H), 2.45 (m, 4H), 2.27 (m, 1H), 1.46 (m, 5H), 0.90 (t, 6H, J=7.3 Hz). ($^{13}$C, ppm, CDCl$_3$): 169.0, 145.0, 138.2, 135.8, 134.1, 133.2, 131.0, 128.6, 127.3, 117.5, 113.9, 106.3, 58.4, 56.9, 52.7, 37.7, 29.3, 27.9, 22.5, 11.7.
M.S.: m/e=387.
U.V.: $\lambda_{max}$=304 ($\epsilon$=19600), 287 ($\epsilon$=19800), 225 ($\epsilon$=23000) in EtOH.
Analysis: Theory: C, 77.47; H, 7.55; N, 10.85; Found: C, 77.09; H, 7.65; N, 10.74.
$[\alpha]_D$=+1.59 (589 nm).

B. Alternative Procedure

The bromide starting material (441 mg, 1 mmole), KCN (100 mg, 1.5 mmole), triphenylphosphine (52 mg, 0.2 mmole), Zn dust (20 mg, 0.3 mmole) and NiBr$_2$[P(C$_6$H$_5$)$_2$]$_2$ (74 mg, 0.1 mmole) was combined in a dry three neck 25 ml round bottom flask equipped with a condenser topped with a nitrogen inlet, and rubber septa on the other necks. The reaction vessel was then degassed several times by repeated vacuum/nitrogen purge cycles. Freshly distilled THF (5 ml) was then added via syringe and the flask was stirred at 60° C. (oil bath temp). The initially green solution became orange/brown over a 30 minute period. The reaction progress was monitored by HPLC and TLC. After 7 hours, HPLC incated only 2% starting material remained. After a total of 9 hours, the reaction mixture was allowed to cool to room temperature overnight. The reaction became nearly colorless. The insoluble material was removed by filtration through diatomaceous earth ("Hy-flo") (1 g) and washed thoroughly with tetrahydrofuran (THF) (4×5 ml). The THF solution was transferred to a three-necked flask and treated dropwise with n-butyllithium as described in Example 7.

EXAMPLE 6

Preparation of (2aS,4R)-1-benzoyl-4-(di-n-propyl)amino-6-cyano-1,2,2a,3,4,5-hexahydrobenz[c,d]indole The procedure of Example 5A was followed using (2aS,4R)-1-benzoyl-4-(di-n-propyl)amino-6-bromo-1,2,2a,3,4,5-hexahydrobenz[c,d]indole to provide the named compound.

EXAMPLE 7

Preparation of (2aR,4S)-4-(di-n-propyl)amino-6-cyano-1,2,2a,3,4,5-hexahydrobenz[cd]indole (2aR,4S)-1-Benzoyl-4-(di-n-propyl)amino-6-cyano-1,2,2a,3,4,5-hexahydrobenz[cd]indole (41.02 g, 0.106 mol) was dissolved in freshly distilled THF (375 ml) and cooled to −78° C. with dry ice-acetone under nitrogen. n-Butyllithium (59.3 ml, 0.148 mole, 1.6 mole equivalent, 2.5M) was then added dropwise at a rate to maintain the temperature below −65° C. When thin layer chromatography analysis indicated complete reaction, glacial acetic acid (10 ml) was added carefully and the reaction mixture was warmed to room temperature. Ethyl ether (250 ml) and 1N HCl (250 ml) were added and the layers separated. The organic phase was extracted with additional 1N HCl (2×100 ml), and the combined aqueous phase washed with ethyl ether (2×250 ml). 5N NaOH (90–100 ml) was added dropwise with stirring followed by extraction with $CH_2Cl_2$ (250+2×150 ml). The combined organic phase was washed with brine, dried over $Na_2SO_4$ and concentrated to dryness. The resulting light tan, highly crystalline material was dried in vacuo to a constant weight (28.4 g, 94.5%). This material was recrystallized from hot aqueous ethanol (ethanol:$H_2O$=75:25), cooled, filtered and washed with ice cold solvent.

m.p.: 113°–114° C.

IR: 3336, 2934, 2210, 1625, 1586, 805 cm$^{-1}$.

NMR: ($^1$H, ppm, $CDCl_3$): 7.27 (1H, d, J - 9.0 Hz), 6.39 (1H, d, J=9.0 Hz), 4.12 (1H, br s), 3.75 (1H, m) 3.20 (1H, m), 3.03 (1H, dd, J - 18, 6.0 Hz), 2.63 (1H, ddd, J=18, 12, 2.0 Hz), 2.45 (4H, t, J=9.0 Hz), 2.19 (1H, dt, J=6.0, 3.0 Hz), 1.45 (5H, m), 0.89 (6H, t, J=9.0 Hz). ($^{13}$C, ppm, $CDCl_3$): 154.0, 137.4, 134.0, 130.7, 119.2, 105.7, 99.6, 57.4, 55.7, 52.8, 38.9, 29.7, 27.6, 22.6, 11.8.

M.S.: m/e=283, 254, 240, 183, 156, 128, 98, 72.

U.V.: $\lambda_{max}$=296 ($\epsilon$=16500), 231 ($\epsilon$=14100, 205 ($\epsilon$16300) in EtOH.

Analysis: Theory: C, 76.28; H, 8.89; N, 14.83. Found: C, 76.56; H, 8.85; N, 14.71.

$[\alpha]_D$= −34.0 (589 nm), THF, c=0.01.
$[\alpha]_D$= −217.7 (365 nm).

EXAMPLE 8

Preparation of (2aS,4R)-4-(di-n-propyl)amino-6-cyano-1,2,2a,3,4,5-hexahydrobenz[c,d]indole The procedure of Example 7 was followed using (2aS,4R)-1-benzoyl-4-(di-n-propyl)amino-6-cyano-1,2,2a,3-4,5-hexahydrobenz[c,d]indole to provide the title compound.

EXAMPLE 9

Preparation of (2aR,4S)-4-(di-n-propylamino)-6-amino-carbonyl-1,2,2a,3,4,5-hexahydrobenz[c,d]indole Polyphosphoric acid (PPA, 300 ml) was placed into a 500 ml three neck flask equipped with a mechanical stirrer, a stopper and a condenser topped with a nitrogen inlet. The reaction vessel was degassed by vacuum/purge cycles (5×). The flask was then heated to 85°–90° C. (internal temp) and (2aR,4S)-4-(di-n-propyl)amino-6-cyano-1,2,2a,3,4,5-hexahydrobenz[cd]indole (22.65 g, 0.080 mole) was added portionwise. The reaction mixture became homogeneous as the hydrolysis occurred. After all of the nitrile had been added, the mixture was stirred at this temperature for an additional 2.0 hours to ensure complete hydrolysis. The reaction mixture was then carefully poured onto crushed ice and stirred vigorously. After the ice had melted, the pH was adjusted with 5N NaOH to 11–12 and extracted with several portions of $CH_2Cl_2$. The organic phase was dried over sodium sulfate, filtered and concentrated to afford 23.53 g of the amide as a foam.

m.p.=161°–164 ° C.

IR: (KBr): 3392 (br), 3180 (br), 2957 (m), 2934 (m), 2870 (w), 2810 (w), 1654 (s), 1584 (s), 1457 (s), 1380 (s), 1350 (s) cm$^{-1}$.

NMR: ($^1$H, ppm, $CDCl_3$): 7.30 (d, 1H), 6.40 (d, 1H), 5.7 (brs, 2H), 3.9 (m, 1H), 3.70 (m, 1H), 3.05–3.30 (m, 4H), 2.85 (dd, 1H), 2.45 (m, 4H), 2.15 (m, 1H), 1.45 (m, 4H), 0.90 (t, 6H).

IR: 3381 (s), 3377 (s), 2956 (m), 2932 (m), 1645 (s), 1616 (s), 1585 (m), 1379 (s) cm$^{-1}$.

M.S.: m/e=301 (fd).

U.V.: $\lambda_{max}$=273 ($\epsilon$=15400), 214 ($\epsilon$=22300) in ethanol.

Analysis: Theory: C, 71.72; H, 9.02; N, 13.94; Found: C, 68.40; H, 8.78; N, 13.73.

$[\alpha]_D$= −70.46 (589 nm) ($CH_3OH$, C=1.02).

EXAMPLE 10

Preparation of (2aS, 4R)-4-(di-n-propyl)-6-aminocarbonyl-1,2,2a,3,4,5-hexahydrobenz[c,d]indole The procedure of Example 1 was followed using (2aS, 4R)-4-(di-n-prozeyl)amino-6-cyano-1,2,2a,3,4,5-hexahydrobenz[c,d]indole to provide the above-titled product.

EXAMPLE 11

Preparation of Methyl (2aS,4R)-4-(Di-n-propylamino)-1,2,2a,3,4,5-hexahydrobenz[c,d]indole-6-carboxylate A. (2aS,4R)-1-(t-Butyloxycarbonyl)-6-iodo-4-(di-n-propylamino)-1,2,2a,3,4,5-hexahydrobenz[c,d]indole A mixture of 10.0 g (20 mmol) of (2aS,4R)-1-benzoyl-6-iodo-4-(di-n-propylamino)-1,2,2a,3,4,5-hexahydrobenz[c,d]indole and 100 ml of 3M $H_2SO_4$ was refluxed under nitrogen for 2.5 hours. After cooling the mixture was filtered and the solid was washed with 1M $H_2SO_4$. The filtrate and washings were combined, washed with $CH_2Cl_2$, and basified with 10N NaOH. The oil that separated was extracted into $CH_2Cl_2$. After drying over $Na_2SO_4$, the solvent was evaporated leaving 6 g of brown oil. Chromatography over 100 g of florisil using ethyl acetate afforded 4.82 g of an oil which by NMR was a 1:2 mixture of (2aS,4R)-6-iodo-4-(di-n-propylamino)-1,2,2a,3,4,5-hexahydrobenz[c,d]indole and the corresponding des-iodo compound. This mixture was dissolved in 25 ml of $CH_2Cl_2$ and treated with 4.0 ml of di-t-butyl dicarbonate. After stirring overnight, the volatile materials were removed under vacuum. The residual oil was-dissolved in a small amount of $CH_2Cl_2$ and warmed briefly in the presence of a few ml of $Na_2CO_3$ solution. The $CH_2Cl_2$ solution was separated and dried over $Na_2SO_4$. The solvent was then evaporated, and the product mixture was chromatographed over silica gel using ethyl acetate/toluene (1:9). The crystalline (2aS,4R)-1-(t-butyloxycarbonyl)-6-iodo-4-(di-n-propylamino)-1,2,2a,3,4,5-hexahydrobenz[c,d]indole was recrystallized from isooctane to provide 1.89 g of product, mp 124°–128° C.

B. Methyl (2aS,4R)-1-(t-butyloxycarbonyl)-4-(di-n-propylamino)-1,2,2a,3,4,5-hexahydrobenz[c,d]indole-6-carboxylate A solution of 0.50 g (1.03 mmol) of (2aS,4R)-1-(t-butyloxycarbonyl)-6-iodo-4-(di-n-propylamino)-1,2,-2a,3,4,5-hexahydrobenz[c,d]indole, 0.5 ml of triethylamine, and 50 mg of $(Ph_3P)_4Pd$ in 100 ml of methanol was heated at 55°–60° C. under an atmosphere of CO for 20 hours. After allowing to cool, the solvent was evaporated under reduced pressure. The residual oil was dissolved in CH$_2$Cl$_2$ containing 5% methanol. This solution was then washed with NaCl solution and the CH$_2$Cl$_2$ evaporated. A solution of the residue in 25 ml of methanol was treated with 3% H$_2$O$_2$ solution. After 30 minutes, a fine black precipitate was filtered off. The filtrate was diluted with water and extracted with CH$_2$Cl$_2$. The extract was dried over Na$_2$SO$_4$, then evaporated. The residual oil was chromatographed over 15 g of silica gel using first 1:9 ethyl acetate/toluene (1:9) mixture than a (1:4) mixture. 1:4 EtOAc/toluene. A few of the product-containing fractions from the column were contaminated with Ph$_3$P. These fractions were further purified by partitioning between dilute tartaric acid and CH$_2$Cl$_2$, basifying the aqueous layer with 1N NaOH, and extracting with CH$_2$Cl$_2$. The total yield of methyl (2aS,4R)-1-(t-butyloxycarbonyl)-4-(di-n-propylamino)-1,2,2a,3,4,5-hexahydrobenz[c,d]indole-6-carboxylate, a viscous oil, was 0.415 g (97%).

A solution of 0.284 g (0.68 mmol) of methyl (2aS,4R)-1-(t-butyloxycarbonyl)-4-(di-n-propylamino)-1,2,2a,3,4,5-hexahydrobenz[c,d]indole-6-carboxylate in 3 ml of trifluoroacetic acid was allowed to stand for 1 hour. The excess acid was evaporated under vacuum. The residual oil was dissolved in CH$_2$Cl$_2$. After washing this solution with 1N NaOH, the product was extracted in dilute tartaric acid (3 portions). This aqueous solution was basified with 1N NaOH, and the product was extracted into CH$_2$Cl$_2$. Evaporation of the Na$_2$SO$_4$ dried extract gave 0.214 g (95% yield) of methyl (2aS,4R)-4-(di-n-propylamino)-1,2,2a,3,4,5-hexahydrobenz[c,d]indole-6-carboxylate as a viscous oil.

Analysis (C$_{19}$H$_{28}$N$_2$O$_2$): Theory: C, 72.12; H, 8.92; N, 8.85; Found: C, 72.30; H, 9.09; N, 8.94.

NMR: (300 MHz, CDCl$_3$) δ 0.89 (t, 6H, CCH$_3$), 1.41 (dd, 1H, 3α-H), 1.48 (sextet, 4H, CH$_2$Me), 2.17 (br d, 1H, 3β-H), 2.49 (mult, 4H, CH$_2$Et), 2.85 (dd, 1H, 5α-H), 3.14 (mult, 1H, 2aH), 3.19 (mult, 2H, 2α-H & 2β-H), 3.41 (dd, 1H, 5β-H), 3.72 (mult, 1H, 4-H), 3.82 (s, 3H, OCH$_3$), 3.98 (br s, 1H, 1-H), 6.43 (d, 1H, 8-H), 7.80 (d, 1H, 7-H).

EXAMPLE 12

Preparation of (2aS,4R)-N,N-Dimethyl-4-(di-n-propylamino)-1,2,2a,3,4,5-hexahydrobenz[cd]indole-6-carboxamide A. (2aS,4R)-N,N-Dimethyl-1-(t-butyloxycarbonyl)-4-(di-n-propylamino)-1,2,2a,3,4,5-hexahydrobenz[cd]indole-6-carboxamide A solution of 0.50 g (1.03 mmol) of (2aS,4R)-1-(t-butyloxycarbonyl)-6-iodo-4-(di-n-propylamino)-1,2,2a,3,4,5-hexahydrobenz[c,d]indole (see previous example), 5 g of dimethylamine, and 50 mg of (Ph$_3$P)$_4$Pd in 100 ml of toluene was heated in an autoclave under CO at 100 psi for 8 hours at 100° C. When the resulting clear, yellow solution was washed with NaCl solution a colorless precipitate separated. This precipitate was collected on a filter and thoroughly washed with ethylacetate containing 5% methanol. These washings were combined with the original toluene solution. The solvents were evaporated under reduced pressure. The residual oil was dissolved in 25 ml of methanol and treated with a few ml of 3% H$_2$O$_2$. After 30 minutes the solution was filtered, diluted with water, and extracted with CH$_2$cl$_2$. The extract was dried over Na$_2$SO$_4$ then evaporated under reduced pressure. The residue was chromatographed over 15 g of silica gel using successively 1:9 ethyl acetate/toluene, 1:4 ethyl acetate/toluene, 2:3 ethyl acetate/toluene, and 100% ethyl acetate. As in the previous example a few of the product-containing fractions required further purification by partitioning between CH$_2$Cl$_2$ and aqueous tartaric acid. The total yield of (2aS,4R)-N,N-dimethyl-1-(t-butyloxycarbonyl)-4-(di-n-propylamino)-1,2,2a,3,4,5-hexahydrobenz[cd]indole-6-carboxamide was 0.184 g (42%).

B. A solution of 0.162 g (0.38 mmol) of (2aS,4R)-N,N-dimethyl-1-(t-butyloxycarbonyl)-4-(di-n-propylamino)-1,2,2a,3,4,5-hexahydrobenz[c,d]indole-6-carboxamide in 3 ml of trifluoroacetic acid was allowed to stand for 1 hour. The excess acid was evaporated under vacuum. The residual oil was dissolved in CH$_2$Cl$_2$. After washing this solution with 1 N NaOH, the product was extracted into dilute tartaric acid (3 portions). This aqueous solution was basified with 1N NaOH, and the product was extracted into CH$_2$Cl$_2$. Evaporation of the Na$_2$SO$_4$ dried extract gave 0.110 g (89% yield) of (2aS,4R)-N,N-dimethyl-4-(di-n-propylamino)-1,2,2a,3,4,5-hexahydrobenz[c,d]indole-6-carboxamide as a viscous oil.

Analysis (C$_{20}$H$_{31}$N$_3$O) for: Theory: C, 72.91; H, 9.48; N, 12.75; Found: C, 73.02; H, 9.47; N, 12.88.

NMR: (300 MHz, CDCl$_3$) δ 0.88 (t, 6H, CCH$_3$), 1.40 (dd, 1H, 3α-H), 1.46 (sextet, 4H, CH$_2$Me), 2.18 (br d, 1H, 3β-H), 2.45 (octet, 4H, CH$_2$Et), 2.63 (dd, 1H, 5α-H), 2.77 (dd, 1H, 5β-H), 2.94 (br s, 3H, NCH$_3$), 3.07 (br s, 3H, NCH$_3$), 3.15 (mult, 3H, 2α-H & 2β-H & 2a-H), 3.68 (mult, 1H, 4-H), 6.43 (d, 1H, 8-H), 6.86 (d, 1H, 7-H).

The compounds have been found to have selective affinity for 5-HT$_{1A}$ receptors with much less affinity for other receptors. Because of their ability to selectively interact with 5-HT$_{1A}$ receptors, the compounds of Formula (I) are useful in treating disease states which require alteration of 5-HT$_{1A}$ function but without the side effects which may be associated with less selective compounds. This alteration may involve reproducing (an agonist) or inhibiting (an antagonist) the function of serotonin. These disease states include anxiety, depression, hypertension, acid secretion, sexual dysfunction, motion sickness, nausea, senile dementia (cognition), and consumptive disorders such as obesity, alcoholism, drug abuse and smoking. A pharmaceutically effective amount of a compound of Formula (I) is required to treat the foregoing conditions.

The term "pharmaceutically effective amount", as used herein, represents an amount of a compound of the invention which is capable of diminishing the adverse symptoms of the particular disease. The particular dose of compound administered according to this invention will of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. A typical single dose for prophylactic treatment, however, will contain from about 0.01 mg/kg to about 20 mg/kg of the active compound of this invention when administered orally. Preferred oral doses will be about 0.5 to about 10 mg/kg, ideally about 1.0 to about 5 mg/kg. When a present compound is given orally it may be necessary to administer the compound more than once each day, for example about every eight hours. For IV administration by bolus, the dose will be from about 1.0

μg/kg to about 3000 μg/kg, preferably about 50 μg/kg to about 500 μg/kg.

The following experiment was conducted to demonstrate the ability of the compounds of the present invention to interact with the serotonin 1a receptors. This general procedure is set forth in Wong et al., *J. Neural Transm.* 71:207-218 (1988).

Male Sprague-Dawley rats (110-150 g) from Harlan Industries (Cumberland, IN) were fed a Purina Chow ad libitum for at least 3 days before being used in the studies. Rats were killed by decapitation. The brains were rapidly removed, and the cerebral cortices were dissected out at 4° C.

Brain tissues were homogenized in 0.32M sucrose. After centrifugation at 1000×g for 10 min then at 17000×g for 20 min, a crude synaptosomal fraction was sedimented. The pellet was suspended in 100 vol of 50 mM Tris-HCl, pH 7.4, incubated at 37° C. for 10 min, and centrifuged at 50000×g for 10 min. The process was repeated and the final pellet was suspended in ice-chilled 50 mM Tris-HCl, pH 7.4. By the radioligand binding method, sites specifically labeled by tritiated 8-hydroxy-2-dipropylamino-1,2,3,4-tetrahydronaphthalene ($^3$H-8-OH-DPAT) have been identified as 5-HT$_{1A}$ receptors.

Binding of ($^3$H-8-OH-DPAT) was performed according to the previously described method [Wong et al., *J. Neural Transm.* 64:251-269 (1985)]. Briefly, synaptosomal membranes isolated from cerebral cortex were incubated at 37° C. for 10 min. in 2 ml of 50 mM Tris-HCl, pH 7.4; 10 μM pargyline; 0.6 mM ascorbic acid; 0.4 nM $^3$H-8-OH-DPAT; and from 1 to 1000 mM of test compound. Binding was terminated by filtering samples under reduced pressure through glass fiber (GFB) filters. The filters were washed twice with 5 ml of ice cold buffer and placed in scintillation vials with 10 ml of PCS (Amersham/Searle) scintillation fluid. Radioactivity was measured with a liquid scintillation spectrometer. Unlabeled 8-OH-DPAT at 10 μM was also included in separate samples to establish non-specific binding. Specific binding of $^3$H-8-OH-DPAT is defined as the difference of radioactivity bound in the absence and in the presence of 10 μM unlabeled 8-OH-DPAT.

The results of the evaluation of various compounds of the present invention are set forth below in Table I. In Table I, the first column provides the Example Number of the compound evaluated; and the second column provides the amount of the test compound expressed in nanomolar concentration required to inhibit the binding of $^3$H-8-OH-DPAT) by 50%, and is indicated in Table I as IC$_{50}$. For these compounds which inhibited the binding of $^3$H-8-OH-DPAT by less than 50%, the percent of inhibition is given in parenthesis.

TABLE I

| Example | IC$_{50}$[a] |
|---------|--------------|
| 1 | (6%)[b] |
| 3 | (5%)[b] |
| 5 | (11%)[b] |
| 7 | (21%)[b] |
| 9 | 11 nM |
| 10 | 2.1 nM |
| 11 | 5.7 nM |
| 12 | 5.1 nM |

[a]concentration in nanomoles which inhibited binding of 8-OH-DPAT by 50%
[b]percent of inhibition of binding of 8-OH-DPAT at 100 nanomoles if less than 50%.

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyland propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 1 to about 10 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

FORMULATION 1

Hard gelatin capsules are prepared using the following ingredients:

|  | Quantity (mg/capsule) |
|---|---|
| methyl ester | 25 |
| Starch, dried | 425 |
| Magnesium stearate | 10 |
| Total | 460 mg |

The above ingredients are mixed and filled into hard gelatin capsules in 460 mg quantities.

FORMULATION 2

A tablet formula is prepared using the ingredients below:

|  | Quantity (mg/tablet) |
| --- | --- |
| 4-(di-n-propylamino)-6-amino-carbonyl-1,2,2a,3,4,5-hexahydrobenz[c,d]indole | 25 |
| Cellulose, microcrystalline | 625 |
| Colloidal Silicon dioxide | 10 |
| Stearic acid | 5 |

The components are blended and compressed to form tablets each weighing 665 mg.

FORMULATION 3

A dry powder inhaler formulation is prepared containing the following components:

|  | Weight % |
| --- | --- |
| 4-(diethylamino)-1,2,2a,3,4,5-hexahydrobenz[cd]-indole-6-carboxylic acid, ethyl ester | 5 |
| Lactose | 95 |

The active compound is mixed with the lactose and the mixture added to a dry powder inhaling applicance.

FORMULATION 4

Tablets each containing 60 mg of active ingredient are made up as follows:

| (2aS,4R)-N,N.-Dimethyl-4-(di-n-propylamino)-1,2,2a,3,4,5-hexahydrobenz[c,d]indole-6-carboxamide | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 20 mesh U.S. sieve and mixed thoroughly. The solution of polyvinylpyrrolidone is mixed with the resultant powders which are then passed through a No. 4 mesh U.S. sieve. The granules so produced are dried at 50°–60° C. and passed through a No. 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 150 mg.

FORMULATION 5

Capsules each containing 20 mg of medicament are made as follows:

| (2aS,4R)-4-(di-n-propylamino)-6-aminocarbonyl-1,2,2a,3,4,5-hexahydrobenz-[c,d]indole | 20 mg |
| --- | --- |
| Starch | 169 mg |
| Magnesium stearate | 1 mg |
| Total | 190 mg |

The active ingredient, cellulose, starch and magnesium stearate are blended, passed through a No. 20 mesh U.S. sieve, and filled into hard gelatin capsules in 190 mg quantities.

FORMULATION 6

Suppositories each containing 225 mg of active ingredient are made as follows:

| (2aS,4R)-(Di-n-propylamino)-1,2,2a,3,4,5-hexahydrobenz[c,d]-indole-6-carboxylic acid, methyl ester | 225 mg |
| --- | --- |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions each containing 50 mg of medicament per 5 ml dose are made as follows:

| 4-(di-n-propylamino)-1,2,2a,3,4,5-hexahydrobenz[c,d]indole-6-carbothioic acid. S-methyl ester | 50 mg |
| --- | --- |
| Xanthan Gum | 4 mg |
| Sodium carboxymethyl cellulose (11%) | 50 mg |
| Microcrystalline Cellulose (89%) |  |
| Sucrose | 1.75 g |
| Sodium Benzoate | 10 mg |
| Flavor | q.v. |
| Color | q.v. |
| Purified water to | 5 ml |

The medicament, sucrose and xanthan gum are blended, passed through a No. 10 mesh U.S. sieve, and then mixed with a previously made solution of the microcrystalline cellulose and sodium carboxymethylcellulose in water. The sodium benzoate, flavor and color are diluted with some of the water and added with stirring. Sufficient water is then added to produce the required volume.

FORMULATION 8

Capsules each containing 150 mg of medicament are made as follows:

| 4-(methylamino)-1,2,2a,3,4,5-hexahydrobenz[cd]-indole-6-carboxylic acid, methyl ester | 50 mg |
| --- | --- |
| Starch | 507 mg |
| Magnesium stearate | 3 mg |
| Total | 560 mg |

The active ingredient, cellulose, starch and magnesium stearate are blended, passed through a No. 20 mesh U.S. sieve, and filled into hard gelatin capsules in 560 mg quantities.

What is claimed is:

1. A compound of the Formula

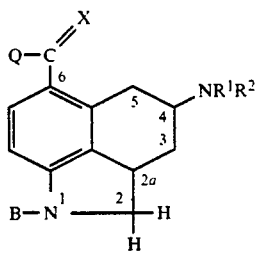

wherein:
- $R^1$ is hydrogen, $C_1$-$C_4$ alkyl, $C_3$-$C_4$ alkenyl, cyclopropylmethyl, phenyl-substituted $C_1$-$C_4$ alkyl, —$COR^4$, —$(CH_2)_nS(C_1$-$C_4$ alkyl) or —$(CH_2)_nCONR^9R^{10}$;
- $R^2$ is hydrogen, $C_1$-$C_4$ alkyl, $C_3$-$C_4$ alkenyl, or cyclopropylmethyl;
- Q is $OR^3$, $SR^3$, $NR^5R^6$ or hydrogen;
- $R^3$ is $C_1$-$C_8$ alkyl, $C_1$-$C_8$ alkyl substituted with one or two moieties independently selected from $C_1$-$C_3$ alkoxy, halo, hydroxy, $C_1$-$C_3$ thioalkyl or nitro, aryl, aryl substituted with one or two moieties independently selected from $C_1$-$C_3$ alkoxy, halo, hydroxy, $C_1$-$C_3$ alkylthio, nitro, $C_1$-$C_3$ alkyl or trifluoromethyl, aryl($C_1$-$C_4$ alkyl), aryl($C_1$-$C_4$ alkyl) substituted with one or two moieties independently selected from $C_1$-$C_3$ alkoxy, halo, hydroxy, $C_1$-$C_3$ alkylthio, nitro, $C_1$-$C_3$ alkyl or trifluoromethyl, or $C_3$-$C_7$ cycloalkyl;
- n is 1-4;
- $R^4$ is hydrogen, $C_1$-$C_4$ alkyl, $C_1$-$C_4$ haloalkyl, $C_1$-$C_4$ alkoxy or phenyl;
- $R^5$ and $R^6$ are independently hydrogen, $C_1$-$C_4$ alkyl substituted with a penyl group, phenyl, or together form a $C_3$-$C_5$ heterocyclic ring, with the proviso that $R^5$ and $R^6$ are not both hydrogen;
- $R^9$ and $R^{10}$ are independently hydrogen, $C_1$-$C_4$ alkyl, or $C_5$-$C_8$ cycloalkyl;
- B is hydrogen, $C_1$-$C_4$ alkyl, or an amino-blocking group;
- X is oxygen or sulfur; or a pharmaceutically acceptable salt thereof.

2. The compound of claim 1 wherein Q is $OR^3$ and X is oxygen; or a pharmaceutically acceptable salt thereof.

3. The compound of claim 1 wherein Q is $NR^5R^6$ and X is oxygen; or a pharmaceutically acceptable salt thereof.

4. The compound of claim 1 wherein Q is $SR^3$ and X is sulfur; or a pharmaceutically acceptable salt thereof.

5. The compound of claim 1 wherein X is oxygen or sulfur;
- $R^1$ is hydrogen, $C_1$-$C_4$ alkyl, allyl, or $C(O)R^4$;
- $R^2$ is hydrogen or $C_1$-$C_4$ alkyl;
- $R^3$ is $C_1$-$C_4$ alkyl;
- $R^4$ is hydrogen, $C_1$-$C_3$ alkyl, trifluoromethyl or phenyl;
- $R^5$ and $R^6$ are independently hydrogen, phenyl ($C_1$-$C_4$ alkyl), phenyl, or together form a $C_3$-$C_5$ heterocyclic ring with the proviso that $R^5$ and $R^6$ are not both hydrogen; or pharmaceutically acceptable salts thereof.

6. The compound of claim 1 wherein:
- $R^1$ and $R_2$ are independently $C_2$-$C_3$ alkyl;
- Q is $OR^3$;
- $R^3$ is $C_1$-$C_4$ alkyl or ($C_1$-$C_3$ alkoxy)substituted $C_1$-$C_4$ alkyl;
- X is oxygen; and
- B is hydrogen, or
- a pharmaceutically acceptable salt thereof.

7. A substantially pure stereoisomer of the compound of claim 1; or a pharmaceutically acceptable salt thereof.

8. The stereoisomer of claim 7 wherein the configuration at position 2a is S and the configuration at position 4 is R; or a pharmaceutically acceptable salt thereof.

9. A method for treating a patient suffering from a disease state in which alteration of 5-$HT_{1A}$ receptor function is beneficial, said method comprising administering to said patient an amount of a compound of claim 1 effective to alter 5-$HT_{1A}$ receptor function.

10. A method for treating a human suffering from anxiety anxiety which comprises administering to said patient an antianxiety dose of a compound of claim 1.

11. A method for treating a human suffering from depression said method comprising administering an antidepressive dose of a compound of claim 1.

12. A method for treating a human suffering from a consumptive disorder said method comprising administering to said human an effective amount of a compound selected from claim 1.

13. A method for treating a patent suffering from a disease state whose symptoms are relieved by altering 5-$HT_{1A}$ receptor function said method comprising administering to said patient an amount of a compound of claim 1 effective to alter 5-$HT_{1A}$ receptor function.

14. A pharmaceutical formulation comprising a compound of claim 1 in combination with a pharmaceutically acceptable excipient.

15. A method for treating a patient suffering from a disease state whose symptoms are relieved by an alteration of 5-$HT_{1A}$ receptor function said method comprising administering to said patient an amount of the formulation of claim 14 effective to releive said symptoms.

* * * * *

UNITED STATES PATENT AND TRADEMARK OFFICE
CERTIFICATE OF CORRECTION

PATENT NO.   : 5,302,612

DATED        : April 12, 1994

INVENTOR(S)  : Michael E. Flaugh, Michael J. Martineli

It is certified that an error appears in the above-identified patent and that said Letters Patent is hereby corrected as shown below:

Claim 1, Column 27, Line 18, delete "$C_1-c_4$ alkyl", and insert therefor --$C_1-C_4$ alkyl--.

Signed and Sealed this

First Day of November, 1994

Attest:

BRUCE LEHMAN

Attesting Officer

Commissioner of Patents and Trademarks